(12) United States Patent
Kang

(10) Patent No.: US 12,293,824 B2
(45) Date of Patent: May 6, 2025

(54) SYSTEM AND METHOD FOR ESTABLISHING DENTAL TREATMENT ENVIRONMENT

(71) Applicant: HEALING SOUND CO., LTD., Seoul (KR)

(72) Inventor: Jun Gu Kang, Seoul (KR)

(73) Assignee: HEALING SOUND CO., LTD., Seoul (KR)

( * ) Notice: Subject to any disclaimer, the term of this patent is extended or adjusted under 35 U.S.C. 154(b) by 450 days.

(21) Appl. No.: 17/781,046

(22) PCT Filed: Nov. 20, 2020

(86) PCT No.: PCT/KR2020/016460
§ 371 (c)(1),
(2) Date: May 31, 2022

(87) PCT Pub. No.: WO2021/112460
PCT Pub. Date: Jun. 10, 2021

(65) Prior Publication Data
US 2022/0415489 A1 Dec. 29, 2022

(30) Foreign Application Priority Data
Dec. 5, 2019 (KR) .......................... 10-2019-0160887

(51) Int. Cl.
G10L 15/08 (2006.01)
G06F 3/16 (2006.01)
(Continued)

(52) U.S. Cl.
CPC ............. *G16H 40/20* (2018.01); *G06F 3/167* (2013.01); *G10L 15/005* (2013.01); *G02B 2027/0141* (2013.01)

(58) Field of Classification Search
CPC . G10L 2015/225; G10L 15/22; G10L 15/063; G10L 15/26; G10L 2015/223;
(Continued)

(56) References Cited

U.S. PATENT DOCUMENTS 10,943,407 B1 * 3/2021 Morgan ................. G16H 15/00
2003/0130016 A1 * 7/2003 Matsuura ............... H04R 5/033
455/569.1

(Continued)

FOREIGN PATENT DOCUMENTS

KR 20-0362466 Y1 9/2004
KR 10-2011-0133089 A 12/2011
(Continued)

OTHER PUBLICATIONS

Kauffmann et al., Machine translation of Chinese publication CN 106164845 A, published Nov. 23, 2016 and filed Apr. 1, 2015, pp. 1-22 ( Year: 2016).*

(Continued)

Primary Examiner — Olujimi A Adesanya
(74) Attorney, Agent, or Firm — Revolution IP, PLLC

(57) ABSTRACT

A system for establishing a dental treatment environment, includes: a head-mounted device provided at a dental clinic to be mounted on a patient's head, the head-mounted device having an image display unit and an ear-mounted speaker, a microphone for converting a sound including the voice of the medical staff in charge of the patient into an electric signal; a voice recognition module for recognizing the voice of the medical staff in charge from the electric sound input from the microphone; a content module storing multiple image contents for relaxing the patient mentally physically; a user interface having a content selection unit configured such that the patient can select a play content provided to the image display unit from the multiple image contents; and an (Continued)

output signal generating module for generating an output signal that is output to the head-mounted device.

8 Claims, 3 Drawing Sheets

(51) Int. Cl.
*G10L 15/00* (2013.01)
*G10L 21/02* (2013.01)
*G16H 40/20* (2018.01)
*G02B 27/01* (2006.01)

(58) Field of Classification Search
CPC ........ G06F 3/167; G06F 3/011; G06F 3/0482; G06F 1/163
See application file for complete search history.

(56) References Cited

U.S. PATENT DOCUMENTS

| | | | |
|---|---|---|---|
| 2005/0186533 A1* | 8/2005 | Cohen | A61G 15/14 433/108 |
| 2006/0136009 A1* | 6/2006 | Staffel | A61N 1/36025 607/46 |
| 2007/0078878 A1* | 4/2007 | Knable | G09B 21/00 |
| 2008/0020361 A1* | 1/2008 | Kron | G09B 23/28 434/262 |
| 2015/0294089 A1* | 10/2015 | Nichols | G16H 10/60 705/3 |
| 2015/0306340 A1* | 10/2015 | Giap | A61B 6/46 600/301 |
| 2016/0183067 A1* | 6/2016 | Auranen | H04W 4/10 398/118 |
| 2018/0197624 A1* | 7/2018 | Robaina | A61B 90/37 |
| 2018/0310384 A1* | 10/2018 | Chang | A61B 90/35 |
| 2020/0066385 A1* | 2/2020 | Newman | G06Q 30/0201 |
| 2022/0387747 A1* | 12/2022 | Kang | H04R 3/04 |
| 2023/0055191 A1* | 2/2023 | Kang | H04R 3/007 |

FOREIGN PATENT DOCUMENTS

| | | |
|---|---|---|
| KR | 10-1351264 B1 | 1/2014 |
| KR | 10-2016-0052517 A | 5/2016 |
| KR | 10-1830908 B1 | 2/2018 |
| KR | 10-2019-0023143 A | 3/2019 |

OTHER PUBLICATIONS

Park et al., Machine translation of Chinese publication CN 102473405 AA, published May 23, 2012 and filed Jul. 10, 2010, pp. 1-30 (Year: 2012).*

International Search Report for PCT/KR2020/016460 mailed Feb. 25, 2021 from Korean Intellectual Property Office.

Reporter Lee, Seung-Jae, [Yonsei University Startup 30] Healing sound, Is Dentistry a Scary Place? Blocking Hospital Noise and Dreaming of Changing the Medical World. Campus Job&Joy.). [online]. Retrieved from the Internet: <URL: http://www.jobnjoy.com/portal/job/special_view.jsp?nidx=280236&depth2=3&depth3=1>, May 16, 2018.

* cited by examiner

SYSTEM AND METHOD FOR ESTABLISHING DENTAL TREATMENT ENVIRONMENT

TECHNICAL FIELD

The present invention relates to a system and method for establishing a dental treatment environment, whereby a patient is mentally physically relaxed and the voice of a medical staff is effectively transmitted to the patient.

BACKGROUND ART

It is very significant to create a comfortable and comfortable environment for treating patients. A quiet environment may be provided to a patient depending on how a disease is treated, whereas in the dental field, sharp and high-frequency noise generated during a treatment process may create discomfort or fear in the patient. However, measures to protect patients exposed to such high-frequency noise are insufficient.

Meanwhile, Korean Utility-model Registration No. 20-0362466 discloses a dental unit chair capable of providing sound and an image so that psychological anxiety that can be felt at the dentist can be relieved. In the technology disclosed in the prior-art patent document, an image is simply provided to the patient through a liquid crystal display (LCD) monitor installed at the dental unit chair.

DETAILED DESCRIPTION OF THE INVENTION

Technical Problem

The present invention provides a system and method for establishing a dental treatment environment, whereby a patient is mentally physically relaxed and the voice of a medical staff in charge of the patient is effectively transmitted to the patient.

Technical Solution

According to an aspect of the present invention, there is provided a system for establishing a dental treatment environment, the system including a head-mounted device provided at a dental clinic to be mounted on a patient's head, the head-mounted device having an image display unit and an ear-mounted speaker, a microphone for converting a sound including a voice of a medical staff in charge of the patient into an electric signal, a voice recognition module for recognizing the voice of the medical staff in charge from the electric sound input from the microphone, a content module for storing a plurality of image contents for relaxing the patient mentally physically, a user interface having a content selection unit configured such that the patient is able to select a play content provided to the image display unit from the plurality of image contents, and an output signal generating module for generating an output signal that is output to the head-mounted device, wherein the output signal generating module generates the output signal including a voice signal of the medical staff in charge when the voice of the medical staff in charge is recognized from the voice recognition module while the output signal is generated from the play image.

According to another aspect of the present invention, there is provided a method for establishing a dental treatment environment using a system for establishing a dental treatment environment, the system including a head-mounted device provided at a dental clinic to be mounted on a patient's head, the head-mounted device having an image display unit and an ear-mounted speaker, a microphone for converting a sound including a voice of a medical staff in charge of the patient into an electric signal, a voice recognition module for recognizing the voice of the medical staff in charge from the electric sound input from the microphone, a content module for storing a plurality of image contents for relaxing the patient mentally physically, a user interface having a content selection unit configured such that the patient is able to select a play content provided to the image display unit from the plurality of image contents, and an output signal generating module for generating an output signal that is output to the head-mounted device, the method including an image selecting operation of selecting a play image provided to the head-mounted device among the plurality of image contents through the user interface, an image outputting operation of outputting the play image selected in the image selecting operation to the image display unit through the output signal generating module, a voice recognition checking operation of checking whether a voice of the medical staff in charge is recognized through the voice recognition module while the play image is output in the image outputting operation, and a voice signal outputting operation of outputting a voice signal of the medical staff in charge to the ear-mounted speaker through the output signal generating module when it is checked that a voice of the medical staff in charge is recognized in the voice recognition checking operation.

Effects of the Invention

According to the present invention, all of the objectives of the present invention described above can be achieved. In detail, because a system for establishing a dental treatment environment including a head-mounted device provided at a dental clinic to be mounted on a patient's head, the head-mounted device having an image display unit and an ear-mounted speaker, a microphone for converting a sound including a voice of a medical staff in charge of the patient into an electric signal, a voice recognition module for recognizing the voice of the medical staff in charge from the electric sound input from the microphone, a content module for storing a plurality of image contents for relaxing the patient mentally physically, a user interface having a content selection unit configured such that the patient is able to select a play content provided to the image display unit from the plurality of image contents, and an output signal generating module for generating an output signal that is output to the head-mounted device, wherein the output signal generating module generates the output signal including a voice signal of the medical staff in charge when the voice of the medical staff in charge is recognized from the voice recognition module while the output signal is generated from the play image and a method for establishing a dental treatment environment using the system are provided, during dental treatment, the patient is able to receive dental treatment in a state where the patient is mentally physically relaxed while watching the patient's preferred image with reduced noise, and the voice of the medical staff in charge can be effectively transmitted to the patient during a treatment process.

In addition, because the voice of the medical staff in charge can be transmitted directly through a character, it is more effective for dental treatment of infants and children.

MODE OF THE INVENTION

Hereinafter, the configuration and operation of embodiments of the present invention will be described in detail with reference to the accompanying drawings.

Figure 1:
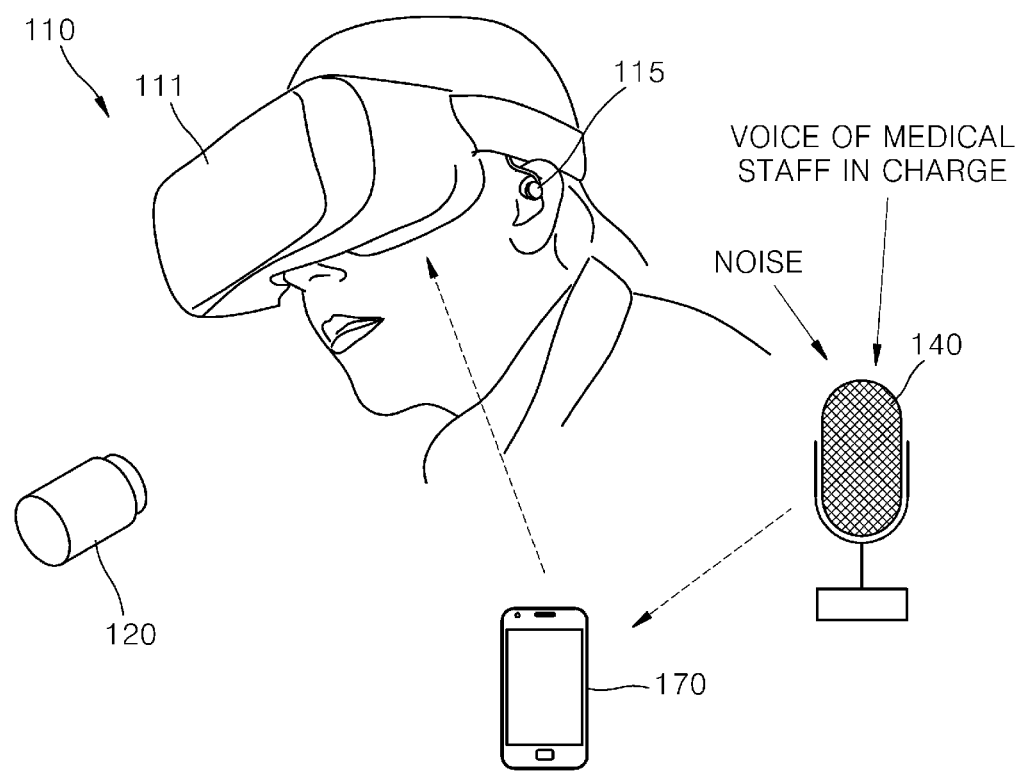
FIG. 1 is a view schematically illustrating elements of a system for establishing a dental treatment environment according to an embodiment of the present invention.
Figure 2:
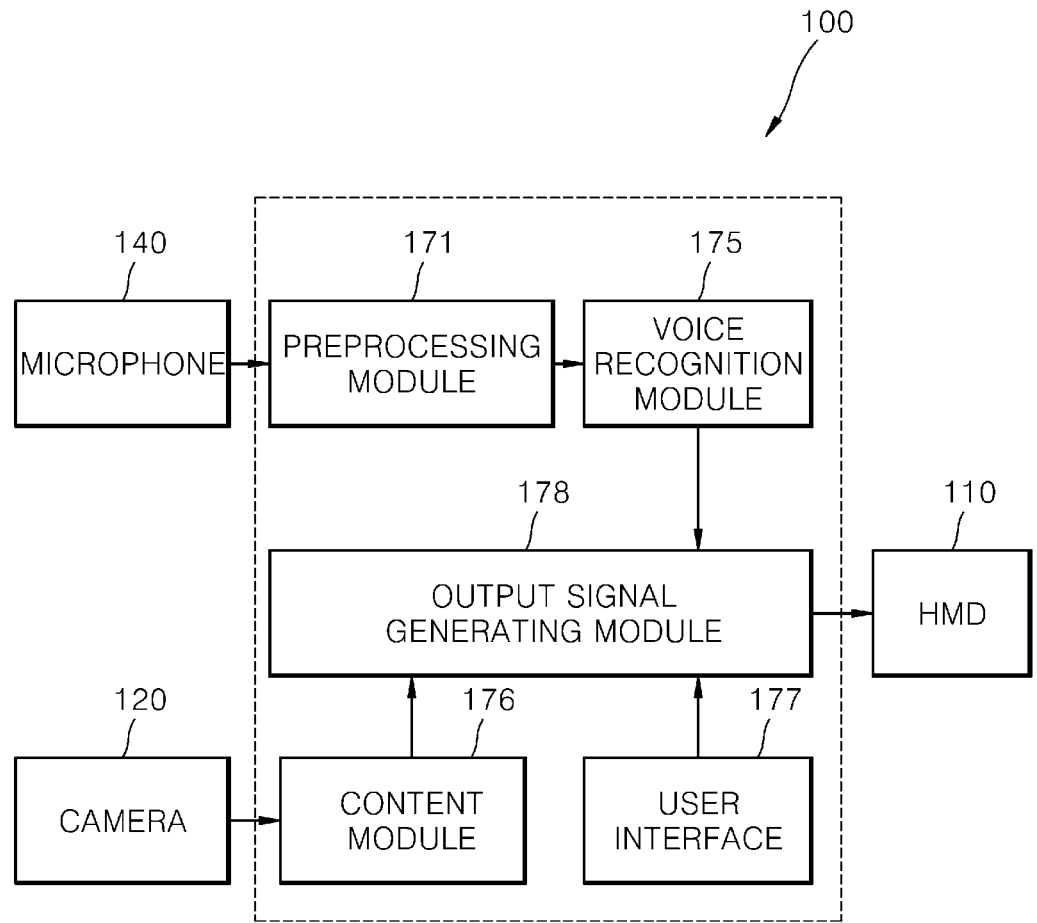
FIG. 2 is a block diagram of the system for establishing a dental treatment environment shown in FIG. 1 according to an embodiment of the present invention.

FIG. 1 is a view schematically illustrating elements of a system for establishing a dental treatment environment according to an embodiment of the present invention, and FIG. 2 is a block diagram of the system for establishing a dental treatment environment shown in FIG. 1 according to an embodiment of the present invention. Referring to FIGS. 1 and 2, a system 100 for establishing a dental treatment environment according to an embodiment of the present invention includes a head-mounted device 110 mounted on a patient's head, a camera 120 for capturing an image of the patient's treatment situation, a microphone 140 for converting an ambient sound including the voice of a medical staff in charge of the patient into an electric signal, and a control device 170 for processing the electric sound signal input from the microphone 140 and outputting an image and a sound signal required for the patient to the head-mounted device 110.

The head-mounted device 110 has a structure in which the patient may wear the head-mounted device 110 on his/her own head, and includes an image display unit 111 for displaying the image transmitted from the control device 170 so that the patient may see the image, and an ear-mounted speaker 115 for converting the electric sound signal transmitted from the control device 170 into a sound wave so that the patient may hear the sound wave. When the patient wears the head-mounted device 110 on his/her own head, the image display unit 111 is located in front of the patient's eyes and displays the image to the patient, and the ear-mounted speaker 115 is mounted on the patient's ears to block unnecessary noise and provide necessary sound to the patient. The image display unit 111 may be implemented with a general image display unit such as a head mounted display (HMD) or a virtual reality (VR), and the ear-mounted speaker 115 may be implemented with a general headphone or earphone. The head-mounted speaker 110 is connected to the control device 170 so as to be capable of communicating with the control device 170 using various wired/wireless communication technologies, and in the present embodiment, it will be described that the head-mounted speaker 110 is connected to the control device 170 using short-range wireless communication technology such as Bluetooth. Although not shown, the head-mounted device 110 may further include a motion sensor mounted on the head-mounted device 110. The motion sensor mounted on the head-mounted device 110 detects the movement of the head-mounted device 110 to transmit data regarding the detected movement of the head-mounted device 110 to the control device 170. In the present embodiment, it will be described that the motion sensor mounted on the head-mounted device 110 is an acceleration sensor.

The camera 120 captures an image of the patient's treatment situation during dental treatment and transmits the captured image to the control device 170 in real time. In the present embodiment, it will be described that the camera 120 is installed at a dental treatment chair or Lupe worn by a medical staff in charge of the patient so as to capture an image of the patient's treatment situation. When the camera 120 is installed at the dental treatment chair, the camera 120 is installed together with an illumination unit for illuminating the patient's oral cavity. The treatment situation captured by the camera 120 is provided to the image display unit 111 through the control device 170 so that the patient may check the treatment situation. The camera 120 is connected to the control device 170 using various wired/wireless communication technologies so as to communicate with the control device 170. In the present embodiment, it will be described that the camera 120 is connected to the control device 170 using a short-range wireless communication technology such as Bluetooth.

The microphone 140 converts the ambient sound including the voice of the medical staff in charge of the patient into an electric signal and transmits the electric signal to the control device 170. To this end, the microphone 140 is connected using various wired/wireless communication technologies so as to be capable of communicating with the control device 170, and in the present embodiment, it will be described that the microphone 140 is worn by the medical staff (doctor) in charge of the patient during dental treatment and is used, and the present invention is not limited thereto, and the microphone 140 may also be properly placed around the patient and the medical staff in charge of the patient and used. Also, in the present invention, it will be described that the microphone 140 is an additional device that is separated from the head-mounted device 110 and the control device 170, however, unlike this, the microphone 140 may be integrally combined with the head-mounted device 110, or the microphone installed in the control device 170 may also be used, and this also belongs to the scope of the present invention. Although not shown, a filter for filtering a sound signal having a required frequency band may be installed together so that the filtered sound signal may be transmitted to the control device 170, and this also belongs to the scope of the present invention.

The control device 170 processes the electric sound signal input from the microphone 140, outputs an image necessary for the patient to the image display unit 111, and outputs an electric sound signal corresponding to a sound necessary for the patient to the ear-mounted speaker 115. In the present embodiment, it will be described that the control device 170 is a personal portable communication terminal device such as a smartphone held by the patient, however, the present invention is not limited thereto, and the control device 170 may be an additional device provided by a hospital including a tablet personal computer (PC) that is not the patient's computer, and this also belongs to the scope of the present invention.

Referring to FIG. 2, the control device 170 includes a preprocessing module 171 for preprocessing the electric sound signal transmitted from the microphone 140 and outputting a preprocessed signal, a voice recognition module 175 for recognizing voice from the preprocessed signal output from the preprocessing module 171 and outputting a voice recognition signal, a content module 176 in which a plurality of image contents are stored, a user interface 177 for connecting the control device 170 and a user of the control device 170, and an output signal generating module 178 for generating an output signal based on a content output from the content module 176, an image signal output from the camera 120, and a voice recognition signal output from the voice recognition module 175 in response to setting matters by the user interface 177. The elements of a controller including the preprocessing module 171, the voice recognition module 175, the content module 176, the user interface 177, and the output signal generating module 178 may be implemented via an application program called application in a terminal device such as a smartphone.

Figure 3:
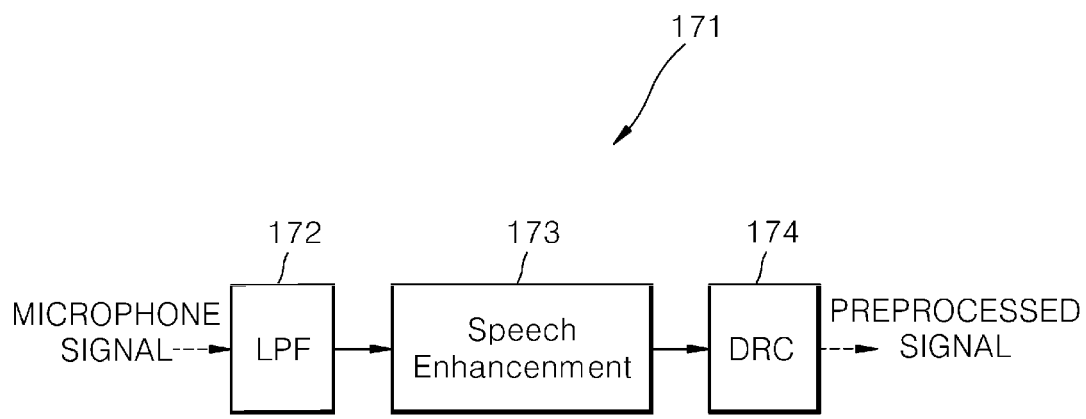
FIG. 3 is a block diagram of the system of a preprocessing unit shown in FIG. 2 according to an embodiment of the present invention.

The preprocessing module 171 preprocesses the electric sound signal transmitted from the microphone 140, removes the sound signal unnecessary for the patient, and outputs a preprocessed signal in which the voice signal is reinforced. FIG. 3 is a block diagram illustrating the elements of the preprocessing module 171 according to an embodiment of the present invention. Referring to FIG. 3, the preprocessing module 171 includes a low pass filter (LPF) 172, a speech enhancement 173, and a dynamic range compressor (DRC) 174.

The LPF 172 passes a low-frequency band and blocks a high-frequency band in the electric sound signal transmitted from the microphone 140, thereby reducing or blocking high-frequency noise distributed in a relatively high-frequency band. A primary processed signal passing through the LPF 172 is transmitted to the speech enhancement 173.

The speech enhancement 173 outputs a secondary processed signal in which background noise is estimated from the primary processed signal output from the LPF 172 and is removed. Because the speech enhancement 173 is technology (e.g., speech enhancement technology disclosed in Registration Patent No. 10-1662946) generally used as a signal processing method for improving the performance of a voice recognition or voice communication system, a detailed description thereof will be omitted.

The DRC 174 outputs a third processed signal in which voice intelligibility is enhanced in the secondary processed signal output from the speech enhancement 173 by using a dynamic range compression (DRC) technique. DRC is to reduce a difference in volume sizes between a portion where the magnitude of a voice signal is large and a portion where the magnitude of a voice signal is small, so as to increase volume while reducing distortion, and for example, a DRC technique disclosed in Registration Patent No. 10-1981487, may be used.

The voice recognition module 175 recognizes specific voice from the preprocessed signal output from the preprocessing module 171 to output a voice recognition signal. The voice recognition module 175 specifically detects the voice of the medical staff in charge of the patient in a noise environment. In the present embodiment, it will be described that the voice recognition module 175 recognizes the voice of the medical staff in charge of the patient by using a general deep learning technology (e.g., a voice recognition method utilizing a deep learning algorithm disclosed in Korean Patent Laid-open Publication No. 10-2019-0074011).

The content module 176 stores a plurality of image contents provided to the patient and provides the image content selected by a user including the patient through the user interface 177 to the output signal generating module 178. The image content stored in the content module 176 includes sound together with an image. The plurality of image contents stored in the content module 176 include virtual reality (VR) three-dimensional (3D) contents. The image contents stored in the contents module 176 include image contents recommended by the medical staff and image contents preferred by the patient, and the content module 176 may be an external application program such as Youtube for providing a video streaming service, in addition to the contents stored in the control device 170, and this also belongs to the scope of the present invention. The content module 176 further includes a plurality of characters. One of the plurality of characters stored in the content module 176 may be selected and used in voice transmission of the medical staff.

Figure 4:
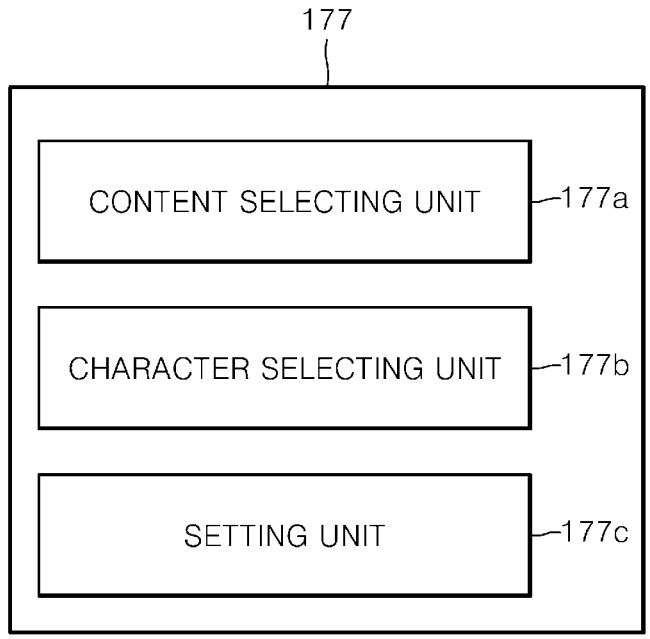
FIG. 4 is a block diagram illustrating the schematic elements of a user interface unit shown in FIG. 2.

The user interface 177 connects between the control device 170 and a user of the control device 170 and the control device 170 so that the user of the control device 170 including the patient may set the control device 170. FIG. 4 illustrates the schematic elements of the user interface 177. Referring to FIG. 4, the user interface 177 includes a content selecting unit 177a, a character selecting unit 177b, and a setting unit 177c.

The content selecting unit 177a visually provides the plurality of image contents stored in the content module 176 to the user so that the user may select one of the plurality of image contents. Also, the content selecting unit 177a may show at least one preferred image content separately stored by the user in addition to the stored image contents. The image content selected by the content selecting unit 177a may be directly played so that the patient may see the image content during dental treatment through the image display unit 111.

The character selecting unit 177b may enable the user including the patient to select a character preferred by the patient from a plurality of characters stored in the content module 176. When the voice of the medical staff is recognized during dental treatment, the character selected by the character selecting unit 177b is output through the image display unit 111, and the voice of the medical staff is transmitted to the patient instead through the ear-mounted speaker 115. This is more effective when the patient is an infant or child. That is, as the infant or pediatric patient's favorite character is output as an image and the guidance voice of the medical staff is transmitted instead, the patient may better follow the medical staff's instructions.

The setting unit 177c provides a window for setting of the control device 170 to the user of the control device 170. The user sets the filtering frequency of the LPF 172, on/off of a noise reduction function, on/off of sound voice playback, and on/off of a voice automatic detection function.

Also, the medical staff confirms the execution of individual operations in a dental treatment process through the user interface 177. For example, wisdom tooth extraction goes through an anesthesia operation, a gum incision operation, a bone preparation operation, a tooth separation operation, a tooth root removal operation, a suturing operation, and the like, and the medical staff confirms the execution of each operation through the user interface 177 immediately before the execution of each operation.

The output signal generating module 178 generates an output signal including an image and a sound based on the content output from the content module 176, the image signal output from the camera 120 and the voice recognition signal output from the voice recognition module 175 in response to the setting matters by the user interface 177. In detail, the output signal generating module 178 provides an image content selected by the user using the content module 176 during dental treatment to the head-mounted device 110 so that the image and the sound signal of the selected image content are output to the image display unit 111 and the ear-mounted speaker 115, respectively, and the patient visually and acoustically enjoys the image content and when the voice of the medical staff is recognized by the voice recognition module 175, the output signal generating module 178 outputs the voice signal of the medical staff to reduce the magnitude of sound included in the image content or eliminate the sound so that the patient may hear the voice of the medical staff through the ear-mounted speaker 115. When the user selects a character, the voice of the medical staff may be transmitted to the patient through the character. Also, when a time in which the voice of the medical staff is not recognized by the voice recognition module 175 continues for a predetermined amount of time or the medical staff speaks a specific sound (e.g., 'end'), the voice recognition module 175 recognizes it and restores the magnitude of sound included in the image content provided by the content module 176 to its original state. Furthermore, the output signal generating module 178 may output a treatment image captured by the camera 120 to the image display unit 111 in real time in addition to the image content stored in the content module 176 according to the user's selection.

Also, the control device 170 detects a sudden movement caused by the patient's pain from the patient's movement during treatment measured by the motion sensor mounted on the head-mounted device 110 and determines the sudden movement. In the present embodiment, it will be described that the control device 170 detects and determines the sudden movement caused by the patient's pain, however, unlike this, the motion sensor mounted on the head-mounted device 110 detects and determines the sudden movement caused by the patient's pain and then, the motion sensor may transmit the sudden movement to the control device 170, and this also belongs to the scope of the present invention. When the sudden movement caused by the patient's pain is detected, the output signal generating module 178 automatically outputs an image relaxing the patient mentally physically to the display unit 111. In this case, the image output to the display unit 111 may include a guide for an operation being executed during a dental treatment process, and the character selected by the patient may be transmitted to the patient.

In the present embodiment, it will be described that the elements of the controller including the preprocessing module 171, the voice recognition module 175, the content module 176, the user interface 177 and the output signal generating module 178 is implemented through an application program installed in the control device 170 that is a terminal device such as a smartphone, however, the present invention is not limited thereto. For example, only the user interface 177 is installed in the control device 170, and the remaining elements (the preprocessing module 171, the voice recognition module 175, the content module 176, and the output signal generating module 178) may be distributed on the head-mounted device 110 or the microphone 140 or may be concentratively installed on any one thereof, and this also belongs to the scope of the present invention.

Figure 5:
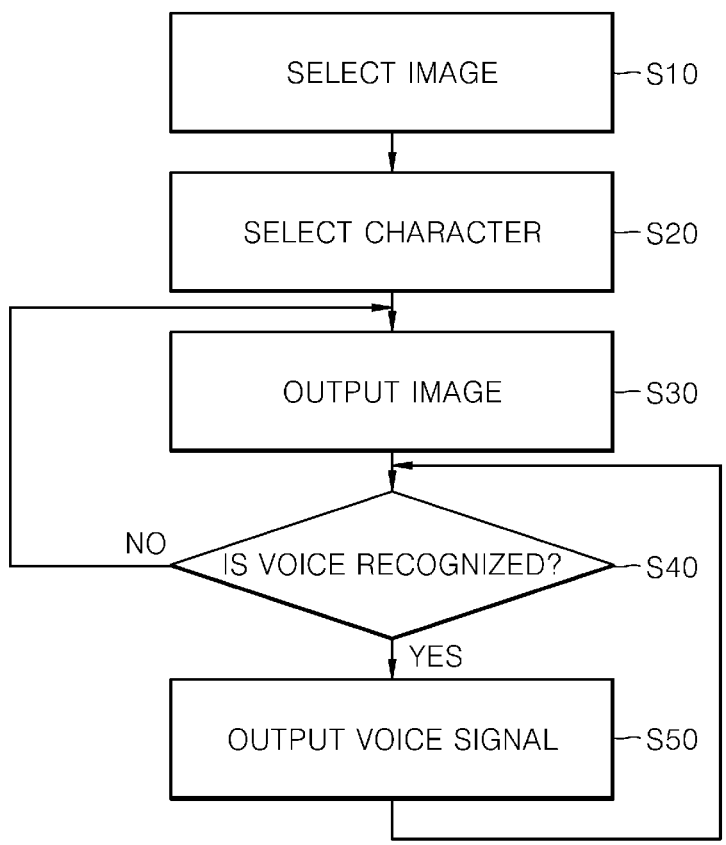
FIG. 5 is a flowchart schematically illustrating a method for establishing a dental treatment environment using the system for establishing a dental treatment environment shown in FIGS. 1 and 2, according to an embodiment of the present invention.

FIG. 5 is a flowchart schematically illustrating a method for establishing a dental treatment environment using the system for establishing a dental treatment environment shown in FIGS. 1 and 2, according to an embodiment of the present invention. Referring to FIG. 5, the method for establishing a dental treatment environment using the system 100 for establishing a dental treatment environment shown in FIGS. 1 and 2 includes an image selecting operation (S10) of selecting an image to be played through the image display unit 111 by using the user interface 177, a character selecting operation (S20) of selecting a character by using the user interface 177, an image outputting operation (S30) of outputting an image selected in the image selecting operation (S10) through the output signal generating module 178, a voice recognition checking operation (S40) of checking whether the voice of a medical staff in charge is recognized through the voice recognition module 175 while the image is output in the image outputting operation (S30), and a voice signal outputting operation (S50) of outputting a voice signal of the medical staff in charge through the output signal generating module 178 when it is checked that the voice of the medical staff in charge is recognized in the voice recognition checking operation (S40).

In the image selecting operation (S10), the image to be played through the image display unit 111 is selected through the user interface 177. The image that may be selected in the image selecting operation (S10) may be one of a plurality of image contents stored in the content module 176 or a treatment image to be captured by the camera 120. The image selecting operation (S10) is performed when the user including the patient selects an image to be played through the user interface 177 by using the control device 170, and the selected image is output to the image display unit 111 in the image outputting operation (S30).

In the character selecting operation (S20), a preferred character is selected through the user interface 177. The character selecting operation (S20) is performed when the user including the patient selects one of a plurality of characters through the user interface 177 by using the control device 170. In the present embodiment, it will be described that the character selecting operation (S20) is performed after the image selecting operation (S10), however, unlike this, the character selecting operation (S20) may be performed before the image selecting operation (S10), and this also belongs to the scope of the present invention. Also, in the present invention, the character selecting operation (S20) may not be performed, and this also belongs to the scope of the present invention.

In the image outputting operation S30, the image selected in the image selecting operation (S10) is output to the image display unit 111 of the head-mounted device 110 through the output signal generating module 178, so that the patient may see the selected image during a dental treatment process. When the image output in the image output operation (S30) includes a sound signal, the image is output to the ear-mounted speaker 115 together with sound so that the patient may hear the sound together with the image.

In the voice recognition checking operation (S40), whether the voice of the medical staff in charge is checked through the voice recognition module 175 while an image is output in the image output operation (S30). The recognition of the voice of the medical staff is the same as the configuration of the preprocessing module 171 and the voice recognition module 175 described above. When the voice of the medical staff in charge of the patient is not checked in the voice recognition checking operation (S30), the image outputting operation (S20) is performed without changes so that the selected image is provided to the patient. When the image output in the image outputting operation (S20) includes sound, the sound having a set magnitude is provided to the patient without changes. When the voice of the medical staff in charge of the patient is checked in the voice recognition checking operation (S40), the voice signal outputting operation (S50) is performed.

In the voice signal outputting operation (S50), when it is checked that the voice of the medical staff in charge is recognized in the voice recognition checking operation (S40), a voice signal of the medical staff in charge is output to the output signal generating module 178. In detail, when it is checked that the voice of the medical staff in charge is recognized in the voice recognition checking operation (S40), the recognized voice signal of the medical staff in charge is transmitted to the ear-mounted speaker 115 through the output signal generating module 178 so that the patient hears the voice of the medical staff in charge through the ear-mounted speaker 178. While the voice of the medical staff in charge is output in the voice signal outputting operation (S50), the volume of sound output in the image outputting operation (S30) is reduced or eliminated, and when sound is eliminated, the image being played may also stop. When a character is selected in the character selecting operation (S20), the selected character appears in the image display unit 111 so that the voice of the medical staff in charge is transmitted to the patient.

While the voice of the medical staff in charge is output in the voice signal outputting operation (S50), the voice recognition operation (S40) is continuously performed, and when the voice of the medical staff in charge is not recognized for a predetermined amount of time in the voice recognition operation (S40) while the voice signal outputting operation (S50) is performed or when a preset specific voice (e.g., 'end') is recognized, the execution of the voice signal outputting operation (S50) is stopped, and the image outputting operation (S30) is performed so that the selected image instead of the voice of the medical staff is provided to the patient together with its original volume.

In addition, in the method for establishing a dental treatment environment, when a sudden movement caused by the patient's pain is detected by the motion sensor mounted in the head-mounted device 110, an operation of automatically outputting an image relaxing the patient mentally physically to the display unit 111 by using the output signal generating module 178. In this case, the image output to the display unit 111 may include a guide for an operation being performed in the dental treatment process, and the character selected by the patient may be transmitted to the patient.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A system for establishing a dental treatment environment, the system comprising:
   a head-mounted device provided at a dental clinic to be mounted on a patient's head, the head-mounted device having an image display unit and an ear-mounted speaker;
   a microphone for converting a sound including a voice of a medical staff in charge of the patient into an electric signal; and
   a controller having a user interface, the controller comprising one or more units and modules being configured and executed by a processor using algorithm, the algorithm which when executed, causing the processor to perform functions using the one or more units and modules, the one or more units comprising:
   a voice recognition module for recognizing the voice of the medical staff in charge from the electric sound input from the microphone;
   a content module for storing a plurality of image contents with sound for relaxing the patient mentally and physically, and a plurality of characters;
   a content selection unit and a character selection unit being included in the user interface, wherein the content selection unit is configured such that the patient is able to select a play content provided to the image display unit and the ear-mounted speaker from the plurality of image contents, wherein the character selection unit is configured such that the patient is able to select one of the plurality of characters: and
   an output signal generating module for generating an output signal that is output to the head-mounted device,
   wherein the output signal generating module stops outputting the play content and generates the output signal including a voice signal of the medical staff in charge through the selected character when the voice of the medical staff in charge is recognized from the voice recognition module while the output signal is generated from the play content,
   wherein in response to a predetermined specific sound of the medical staff in charge being recognized while the play content is stopped, the output signal generating module stops outputting the voice signal of the medical staff in charge through the selected character and resumes outputting the play content.

2. The system of claim 1, further comprising a camera for capturing an image of the patient's treatment situation during dental treatment and transmitting the captured image to the output signal generating module, and the output signal generating module outputs the image captured by the camera as the output signal.

3. The system of claim 1, further comprising a preprocessing module for preprocessing an electric sound signal transmitted from the microphone to transmit the electric sound signal to the voice recognition module, wherein the preprocessing module comprises a low pass filter (LPF) for outputting a primary processed signal in which high-frequency noise is reduced from the electric sound signal transmitted from the microphone, a speech enhancement for removing background noise from the primary processed signal to output a secondary processed signal, and a dynamic range compressor (DRC) for outputting a third processed signal in which voice intelligibility is enhanced from the secondary processed signal using a dynamic range compression technique.

4. The system of claim 1, wherein the voice recognition module recognizes the voice of the medical staff in charge using deep learning.

5. The system of claim 1, wherein the head-mounted device further comprises a motion sensor for measuring movement of the ear-mounted device, and the output signal generating module generates an output signal output to the head-mounted device in response to the movement of the head-mounted device to be measured from the motion sensor.

6. The system of claim 5, wherein the output signal output to the head-mounted device in response to the movement of the head-mounted device comprises a description image for a dental treatment operation being executed by the medical staff in charge and an image relaxing the patient mentally and physically.

7. A method for establishing a dental treatment environment using a system for establishing a dental treatment environment, the system comprising a head-mounted device provided at a dental clinic to be mounted on a patient's head, the head-mounted device having an image display unit and an ear-mounted speaker, a microphone for converting a sound including a voice of a medical staff in charge of the patient into an electric signal, and a controller having a user interface, the controller comprising one or more units and modules being configured and executed by a processor using algorithm, the algorithm which when executed, causing the processor to perform functions using the one or more units and modules, the one or more units comprising a voice recognition module for recognizing the voice of the medical staff in charge from the electric sound input from the microphone, a content module for storing a plurality of image contents with sound for relaxing the patient mentally and physically, and a plurality of characters, a content selection unit and a character election unit being included in the user inter face, the content selection unit is configured such that the patient is able to select a play content provided to the image display unit and the ear-mounted speaker from the plurality of image contents, wherein the character selection unit is configured such that the patient is able to select one of the plurality of characters, and an output signal generating module for generating an output signal that is output to the head-mounted device, the method comprising:

an image selecting operation of selecting the play content provided to the image display unit and the ear-mounted speaker among the plurality of image contents through the content selection unit of the user interface;

a character selecting operation of selecting one of the plurality of characters through the character selection unit;

an image outputting operation of outputting the play content selected in the image selecting operation to the image display unit and the ear-mounted speaker through the output signal generating module;

a voice recognition checking operation of checking whether a voice of the medical staff in charge is recognized through the voice recognition module while the play content is output in the image outputting operation;

a voice signal outputting operation of stopping the output of the play content and generating the output signal to output the voice of the medical staff in charge through the selected character through the output signal generating module when it is checked that a voice of the medical staff in charge is recognized in the voice recognition checking operation; and an operation of stopping outputting the voice signal of the medical staff in charge through the selected character and resuming outputting the play content in response to a predetermined specific sound of the medical staff in charge being recognized while the play content is stopped.

8. The method of claim 7, wherein the head-mounted device further comprises a motion sensor for measuring movement of the head-mounted device, the method further comprising an output signal generating operation of generating an output signal that is output to the head-mounted device in response to the movement of the head-mounted device measured by the motion sensor by using the output signal generating module.

* * * * *